United States Patent
Morobishi (10) Patent No.: US 10,121,456 B2
(45) Date of Patent: Nov. 6, 2018

(54) ELECTRONIC DEVICE, IMAGE DISPLAY METHOD, AND NON-TRANSITORY STORAGE MEDIUM

(71) Applicant: KYOCERA Corporation, Kyoto-shi, Kyoto (JP)

(72) Inventor: Masanori Morobishi, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/194,572

(22) Filed: Jun. 28, 2016

(65) Prior Publication Data

US 2016/0379605 A1 Dec. 29, 2016

(30) Foreign Application Priority Data

Jun. 29, 2015 (JP) ................. 2015-130289

(51) Int. Cl.
  *G09G 5/38* (2006.01)
  *G06F 1/16* (2006.01)
  *G01F 23/26* (2006.01)
  *G06F 3/147* (2006.01)
  *G01N 29/24* (2006.01)

(52) U.S. Cl.
  CPC ............. *G09G 5/38* (2013.01); *G01F 23/263* (2013.01); *G01N 29/24* (2013.01); *G06F 1/1656* (2013.01); *G06F 1/1684* (2013.01); *G06F 1/1694* (2013.01); *G06F 3/147* (2013.01); *G06F 2200/1614* (2013.01); *G09G 2340/04* (2013.01)

(58) Field of Classification Search
  USPC .................................................. 345/173–174
  See application file for complete search history.

(56) References Cited

U.S. PATENT DOCUMENTS

| | | | |
|---|---|---|---|
| 2011/0058085 A1* | 3/2011 | Ito | G03B 13/00 348/333.02 |
| 2012/0146924 A1 | 6/2012 | Inoue | |
| 2015/0036998 A1* | 2/2015 | Ishimaru | H04N 9/8205 386/228 |
| 2016/0054175 A1* | 2/2016 | Jia | G01J 1/4204 250/216 |

FOREIGN PATENT DOCUMENTS

| | | |
|---|---|---|
| JP | 2012-123740 A | 6/2012 |
| JP | 2013-150355 A | 8/2013 |

* cited by examiner

*Primary Examiner* — Ifedayo Iluyomade
(74) *Attorney, Agent, or Firm* — Hauptman Ham, LLP (57) ABSTRACT

An electronic device comprises a display configured to display an image, at least one sensor configured to acquire information, and at least one controller. The at least one controller is configured to detect a first area of the display in contact with water and a second area of the display not in contact with water, and adjust the image so that the image is within the second area when both the first area and the second area are detected.

11 Claims, 12 Drawing Sheets

United States Patent US 10,121,456 B2

ELECTRONIC DEVICE, IMAGE DISPLAY METHOD, AND NON-TRANSITORY STORAGE MEDIUM

CROSS-REFERENCE TO RELATED APPLICATION

The present application claims priority to and incorporates by reference the entire contents of Japanese Patent Application No. 2015-130289 filed in Japan on Jun. 29, 2015.

FIELD

The present application relates to an electronic device, an image display method, and an image display program.

BACKGROUND

Some electronic devices as mobile communication devices are those having a waterproof property. In one specific example, JP-A-2013-150355 discloses a mobile electronic device that ensures a waterproof property by attaching a cap to a housing in which an opening is formed. In other specific example, JP-A-2012-123740 describes that it is configured to disable, when water adhering to a display surface of an input/output module is detected, an acceptance of an operation input related to an operation icon displayed on a display, remove the operation icon from the display, and display that the acceptance is disabled on the display.

SUMMARY

A electronic device, image display method, and non-transitory storage medium are disclosed.

According to one aspect, there is provided an electronic device comprising: a display configured to display an image; at least one sensor configured to acquire information; and at least one controller, wherein the at least one controller is configured to detect a first area of the display in contact with water and a second area of the display not in contact with water, and adjust the image so that the image is within the second area when both the first area and the second area are detected.

According to one aspect, there is provided an image display method for controlling an electronic device with a display, the image display method comprising: detecting a first area of the display in contact with water and a second area of the display not in contact with water, and adjusting the image so that the image is within the second area when both the first area and the second area are detected.

According to one aspect, there is provided a non-transitory storage medium that stores an image display program for causing, when executed by an electronic device with a display, the electronic device to execute: detecting a first area of the display in contact with water and a second area of the display not in contact with water, and adjusting the image so that the image is within the second area when both the first area and the second area are detected.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Exemplary embodiments of an electronic device, a control method, and a control program will be explained in detail below with reference to the accompanying drawings. A smartphone will be explained below as an example of a device provided with a touch screen.

Figure 1:
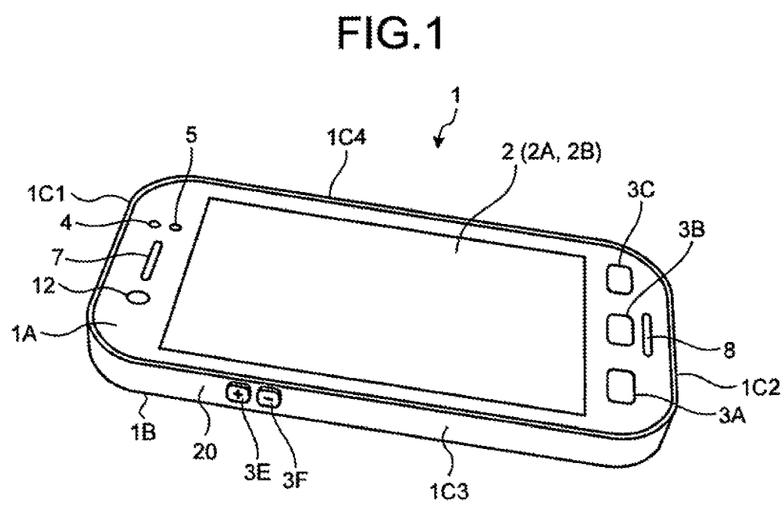
FIG. 1 is a perspective view of a smartphone according to some embodiments.
Figure 2:
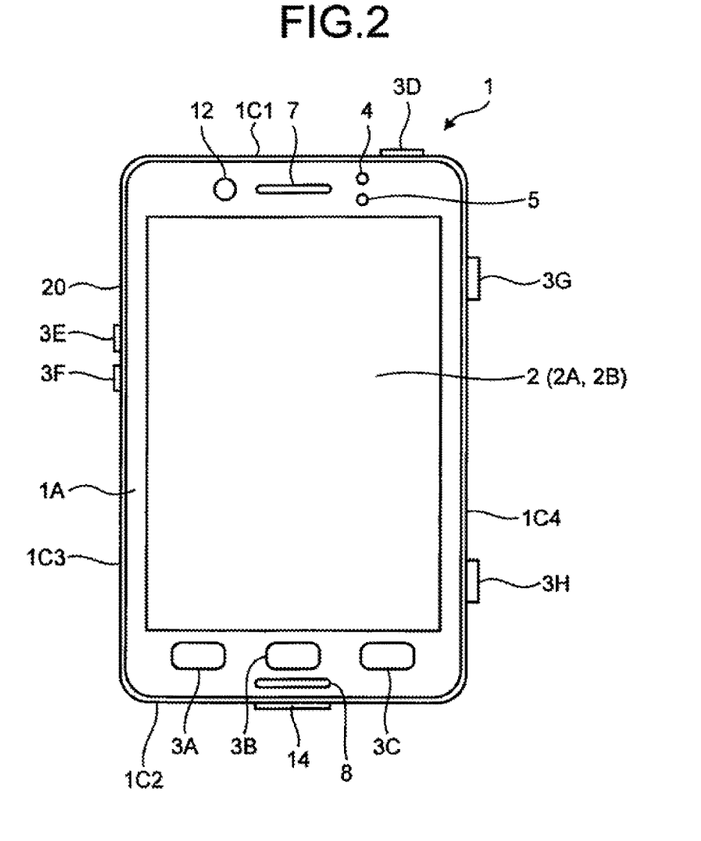
FIG. 2 is a front view of the smartphone.
Figure 3:
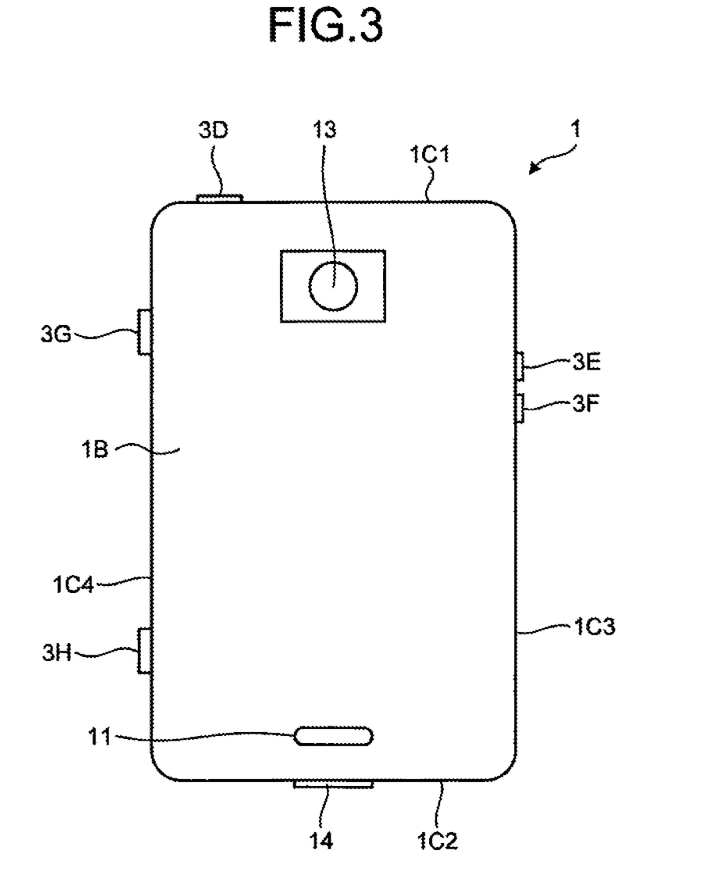
FIG. 3 is a rear view of the smartphone.

The overall configuration of a smartphone 1 according to some embodiments will be explained with reference to FIG. 1 to FIG. 3. As illustrated in FIG. 1 to FIG. 3, the smartphone 1 includes a housing 20. The housing 20 has a structure that suppresses the invasion of water to the inside thereof. The housing 20 has a structure having a waterproof property. Specifically, the housing 20 has a mechanism that passes air but does not pass water disposed at a hole that connects the inside and the outside thereof. When the housing 20 is formed with a plurality of members, the housing 20 has rubber packing or adhesive provided along the boundary of the members. The adhesive is used for sticking the members together. The boundary between the members is hermetically sealed. The housing 20 includes a front face 1A, a rear face 1B, and side faces 1C1 to 1C4. The front face 1A is a front of the housing 20. The rear face 1B is a back of the housing 20. The side faces 1C1 to 1C4 are sides each connecting the front face 1A and the back face 1B. Hereinafter, the side faces 1C1 to 1C4 may be collectively called "side face 1C" without being specific to any of the side faces.

The smartphone 1 includes a touch screen display 2, buttons 3A to 3C, an illumination sensor 4, a proximity sensor 5, a receiver 7, a microphone 8, and a camera 12, which are provided in the front face 1A. The smartphone 1 includes a speaker 11 and a camera 13 provided in the rear face 1B. The smartphone 1 includes buttons 3D to 3H and a connector 14, which are provided in the side face 1C. Hereinafter, the buttons 3A to 3H may be collectively called "button 3" without being specific to any of the buttons.

The touch screen display 2 includes a display 2A and a touch screen 2B. In the example of FIG. 1, each of the display 2A and the touch screen 2B is an approximately rectangular-shaped. However, the shapes of the display 2A and the touch screen 2B are not limited thereto. Each of the display 2A and the touch screen 2B may be any shape such as a square or a circle. In the example of FIG. 1, the display 2A and the touch screen 2B are arranged in a superimposed manner. However, the manner in which the display 2A and the touch screen 2B are arranged is not limited thereto. The display 2A and the touch screen 2B may be arranged, for example, side by side or apart from each other. In the example of FIG. 1, longer sides of the display 2A are along longer sides of the touch screen 2B respectively, and shorter sides of the display 2A are along shorter sides of the touch screen 2B respectively. However, the manner in which the display 2A and the touch screen 2B are superimposed is not limited thereto. If the display 2A and the touch screen 2B are arranged in the superimposed manner, for example, one or more sides of the display 2A do not have to be along any of the sides of the touch screen 2B.

The display 2A is provided with a display device such as a liquid crystal display (LCD), an organic electro-luminescence display (OELD), or an inorganic electro-luminescence display (IELD). The display 2A displays objects such as text, images, symbols, and graphics.

The touch screen 2B detects a contact of a finger, a pen, a stylus pen, or the like on the touch screen 2B. The touch screen 2B can detect positions where a plurality of fingers, pens, stylus pens, or the like make contact with the touch screen 2B. In the description herein below, a finger, a pen, a stylus pen, or the like that contacts with the touch screen 2B may be called "contacting object" or "contacting thing".

The detection method of the touch screen 2B may be any detection method such as a capacitive type detection method, a resistive type detection method, a surface acoustic wave type detection method, an infrared type detection method, and a load sensing type detection method. In the description herein below, for the sake of simplicity, it is assumed that the user uses his/her finger(s) to make contact with the touch screen 2B in order to operate the smartphone 1.

The smartphone 1 determines a type of a gesture based on at least one of a contact detected by the touch screen 2B, a position where the contact is detected, a change of a position where the contact is detected, an interval between detected contacts, and the number of detection times of the contact. The gesture is an operation performed on the touch screen 2B. Examples of the gestures determined by the smartphone 1 include, but are not limited to, touch, long touch, release, swipe, tap, double tap, long tap, drag, flick, pinch in, and pinch out.

Figure 4:
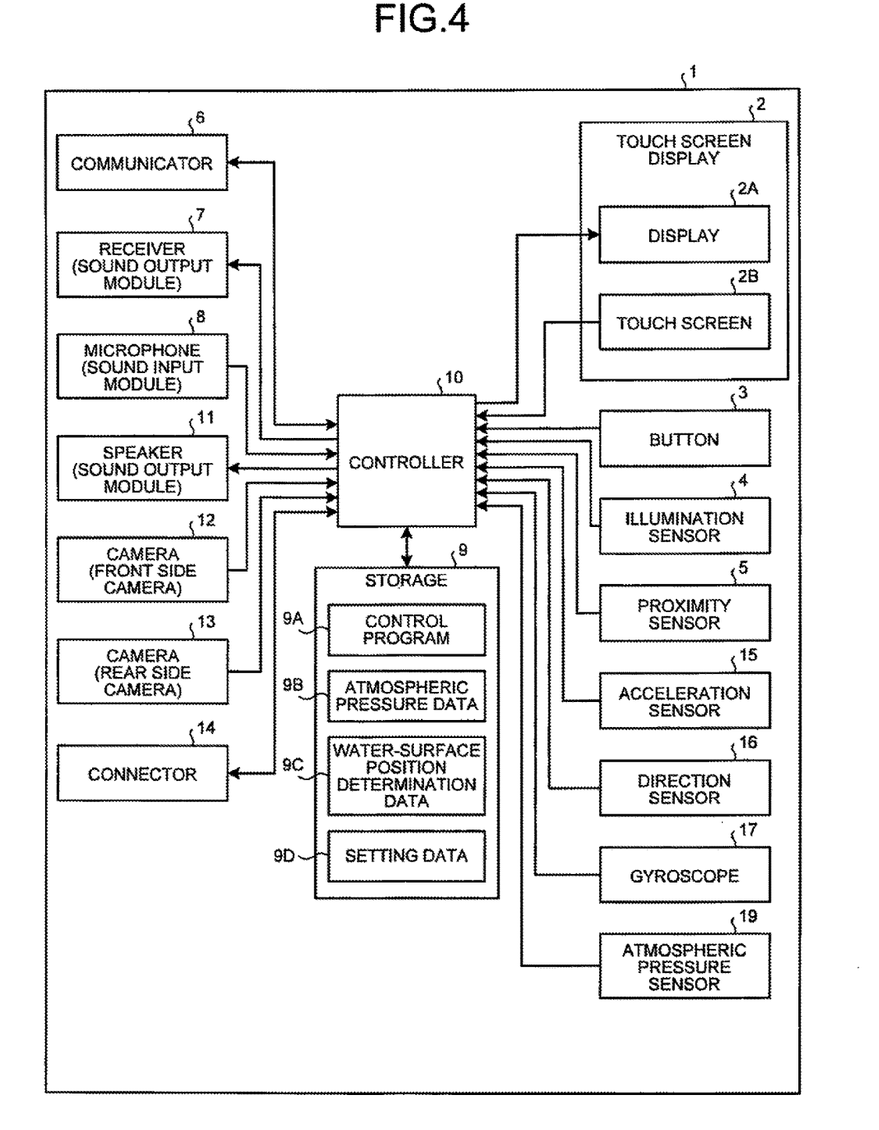
FIG. 4 is a block diagram of the smartphone.

FIG. 4 is a block diagram of the smartphone 1. The smartphone 1 includes the touch screen display 2, the button 3, the illumination sensor 4, the proximity sensor 5, a communicator 6, the receiver 7, the microphone 8, a storage 9, a controller 10, the speaker 11, the cameras 12 and 13, the connector 14, an acceleration sensor 15, a direction sensor 16, a gyroscope 17, and an atmospheric pressure sensor 19.

The touch screen display 2 includes, as explained above, the display 2A and the touch screen 2B. The display 2A displays text, images, symbols, graphics, or the like. The touch screen 2B detects contact(s). The controller 10 detects a gesture for the smartphone 1. Specifically, the controller 10 detects an operation (a gesture) for the touch screen 2B (touch screen display 2) in cooperation with the touch screen 2B.

The button 3 is operated by the user. The button 3 includes buttons 3A to 3H. The controller 10 detects an operation for the button 3 in cooperation with the button 3. Examples of the operations for the button 3 include, but are not limited to, a click, a double click, a triple click, a push, and a multi-push.

The buttons 3A to 3C are, for example, a home button, a back button, or a menu button. The button 3D is, for example, a power on/off button of the smartphone 1. The button 3D may function also as a sleep/sleep release button. The buttons 3E and 3F are, for example, volume buttons. The button 3G is, for example, a power button. The button 3H is, for example, a shutter button. In the present embodiment, the buttons 3E and 3F are provided in the side face 1C3. The buttons 3G and 3H are provided in the side face 1C4. The button 3G is disposed at a position thereof closer to the side face 1C1 side than the button 3H. Accordingly, the button 3H is disposed at a position thereof closer to the side face 1C2 side than the button 3G.

The illumination sensor 4 detects illumination of ambient light of the smartphone 1. The illumination indicates a value of luminous flux incident on a unit area of a measuring surface of the illumination sensor 4. The illumination sensor 4 is used, for example, to adjust brightness of the display 2A. The proximity sensor 5 detects presence of a nearby object in a non-contact manner. The proximity sensor 5 detects the presence of the object based on a change of magnetic field, a change of return time of reflected ultrasonic wave, etc. The proximity sensor 5 detects, for example, approaching of a face to the display 2A. The illumination sensor 4 and the proximity sensor 5 may be configured as one sensor. The illumination sensor 4 can be used as a proximity sensor.

The communicator 6 performs wireless communication. A communication system supported by the communicator 6 includes wireless communication standard. The wireless communication standard includes, for example, a cellular-phone communication standard such as 2G, 3G, and 4G. The cellular-phone communication standard includes, for example, Long Term Evolution (LTE), Wideband Code Division Multiple Access (W-CDMA), CDMA 2000, a Personal Digital Cellular (PDC), a Global System for Mobile Communications (GSM) (registered trademark), and a Personal Handy-phone System (PHS). The wireless communication standard further includes, for example, Worldwide Interoperability for Microwave Access (WiMAX), IEEE 802.11, Bluetooth (registered trademark), Infrared Data Association (IrDA), Near Field Communication (NFC), and a Wireless Personal Area Network (WPAN). The WPAN communication standard includes, for example, Zig- Bee (registered trademark). The communicator 6 may support one or more communication standards. The communicator 6 may support wired communication. The wired communication includes, for example, Ethernet (registered trademark) and fiber channel.

The receiver 7 and the speaker 11 are sound output modules. The receiver 7 and the speaker 11 output a sound signal transmitted from the controller 10 as sound. The receiver 7 is used, for example, to output voice of a partner on calling. The speaker 11 is used, for example, to output a ringtone and music. Either one of the receiver 7 and the speaker 11 may also serve as the other function. The microphone 8 is a sound input module. The microphone 8 converts voice of the user or the like to a sound signal and transmits the sound signal to the controller 10.

The storage 9 stores programs and data. The storage 9 may be used also as a work area that temporarily stores a processing result of the controller 10. The storage 9 may include any non-transitory storage medium such as a semiconductor storage medium and a magnetic storage medium. The storage 9 may include a plurality type of storage mediums. The storage 9 may include a combination of a portable storage medium such as a memory card, an optical disk, or a magneto-optical disk with a reading device of the storage medium. The storage 9 may include a storage device used as a temporary storage area such as Random Access Memory (RAM).

Programs stored in the storage 9 include applications executed in the foreground or the background and a control program for assisting operations of the applications. The application causes the controller 10, for example, to display a screen on the display 2A and perform processing according to a gesture detected through the touch screen 2B. The control program includes, for example, an OS. The applications and the control program may be installed in the storage 9 through communication by the communicator 6 or through a non-transitory storage medium.

The storage 9 stores, for example, a control program 9A, an atmospheric pressure data 9B, a water-surface position determination data 9C, and setting data 9D. The atmospheric pressure data 9B includes information on a relationship between detection result of the atmospheric pressure sensor 19 and a state of the smartphone 1. The atmospheric pressure data 9B stores a relationship between a detection result of the atmospheric pressure sensor 19 previously detected through a test, a simulation, or so and criteria used to determine whether the smartphone 1 is in contact with water. The water-surface position determination data 9C includes information used for estimating how the user moves the smartphone 1. The water-surface position determination data 9C stores a correspondence relationship between a detection result of the sensor previously detected through a test, a simulation, or so and a position of the water surface. The setting data 9D includes information on various settings related to the operations of the smartphone 1.

The control program 9A can provide functions related to various controls for operating the smartphone 1. The control program 9A controls, for example, the communicator 6, the receiver 7, and the microphone 8 to make a phone call. The functions provided by the control program 9A includes functions for performing various controls such as changing of information displayed on the display 2A according to a gesture detected through the touch screen 2B. The functions provided by the control program 9A can be used in combination with a function provided by the other program such as a mail application.

The controller 10 is a processor. Examples of the processor include, but are not limited to, a Central Processing Unit (CPU), System-on-a-chip (SoC), a Micro Control Unit (MCU), and a Field-Programmable Gate Array (FPGA). The controller 10 integrally controls the operations of the smartphone 1 to implement various functions.

Specifically, the controller 10 executes commands included in the program stored in the storage 9 while referring to the data stored in the storage 9 as necessary. The controller 10 then controls a function module according to the data and the commands to implement the various functions. Examples of the function module may include, but are not limited to, at least one of the display 2A, the communicator 6, the receiver 7, and the speaker 11. The controller 10 can change the control according to the detection result of a detector. Examples of the detector may include, but are not limited to, at least one of the touch screen 2B, the button 3, the illumination sensor 4, the proximity sensor 5, the microphone 8, the camera 12, the camera 13, the acceleration sensor 15, the direction sensor 16, the gyroscope 17, and the atmospheric pressure sensor 19.

The controller 10 executes, for example, the control program 9A, and may thereby perform the various controls such as changing of the information displayed on the display 2A according to the gesture detected through the touch screen 2B.

The camera 12 is a front side camera for imaging an object facing the front face 1A. The camera 13 is a rear side camera for imaging an object facing the rear face 1B. The camera 13 is disposed at a position of the rear face 1B close to the side face 1C1 side.

The connector 14 is a terminal to which other device is connected. The connector 14 may be a general-purpose terminal such as a Universal Serial Bus (USB), a High-Definition Multimedia Interface (HDMI) (registered trademark), Light Peak (Thunderbolt (registered trademark)), and an earphone/microphone connector. The connector 14 may be a dedicated terminal such as a dock connector. Examples of the devices connected to the connector 14 include, but are not limited to, an external storage, a speaker, and a communication device.

The acceleration sensor 15 detects a direction and a magnitude of acceleration acting on the smartphone 1. The direction sensor 16 detects a direction of geomagnetism. The gyroscope 17 detects an angle and an angular velocity of the smartphone 1. The atmospheric pressure sensor 19 detects air pressure (atmospheric pressure) outside of the smartphone 1. The atmospheric pressure sensor 19 is positioned inside the housing 20. The internal air pressure in the housing 20 and the external air pressure are equally changed through the hole that does not pass water but passes air. Thereby the atmospheric pressure sensor 19 can detect the external air pressure of the smartphone 1 while being inside of the housing 20. The detection results of the acceleration sensor 15, the direction sensor 16, and the gyroscope 17 may be used in combination with each other in order to detect a position of the smartphone 1 and a change of its attitude.

Part or all of the programs and the data stored in the storage 9 in FIG. 4 may be downloaded from any other device through communication by the communicator 6. Part or all of the programs and the data stored in the storage 9 in FIG. 4 may be stored in a non-transitory storage medium that can be read by a reading device included in the storage 9. Part or all of the programs and the data stored in the storage 9 in FIG. 4 may be stored in a non-transitory storage medium that can be read by a reading device connected to the connector 14. Examples of the non-transitory storage mediums include, but are not limited to, an optical disk such as CD (registered trademark), DVD (registered trademark), and Blu-ray (registered trademark), a magneto-optical disk, magnetic storage medium, a memory card, and solid-state storage medium.

The configuration of the smartphone 1 illustrated in FIG. 4 is one example of embodiments. For example, the number and the type of the button 3 are not limited to the example of FIG. 4. The smartphone 1 may be provided with buttons of a numeric keypad layout or a QWERTY layout as buttons for operation of the screen instead of the buttons 3A to 3C. The smartphone 1 may be provided with only one button to operate the screen, or with no button. In the example illustrated in FIG. 4, the smartphone 1 is provided with two cameras. However, the smartphone 1 may be provided with only one camera or with no camera. In the example of FIG. 4, the smartphone 1 is provided with three types of sensors in order to detect its position and attitude. However, the smartphone 1 does not have to be provided with some of the sensors. Alternatively, the smartphone 1 may be provided with any other type of sensor for detecting at least one of the position and the attitude.

Figure 5:
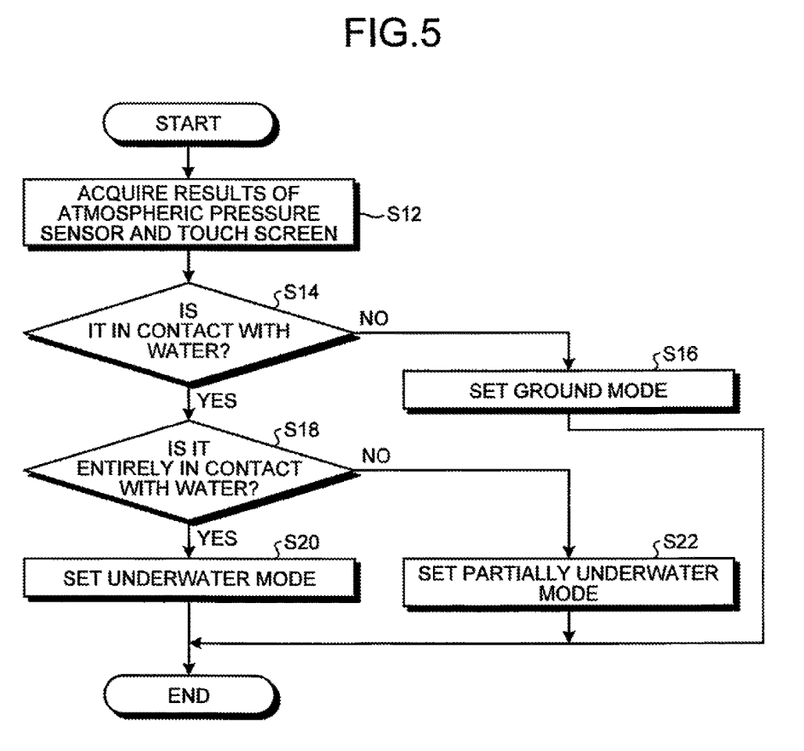
FIG. 5 is a flowchart illustrating an example of control performed by the smartphone according to the embodiments.
Figure 6:
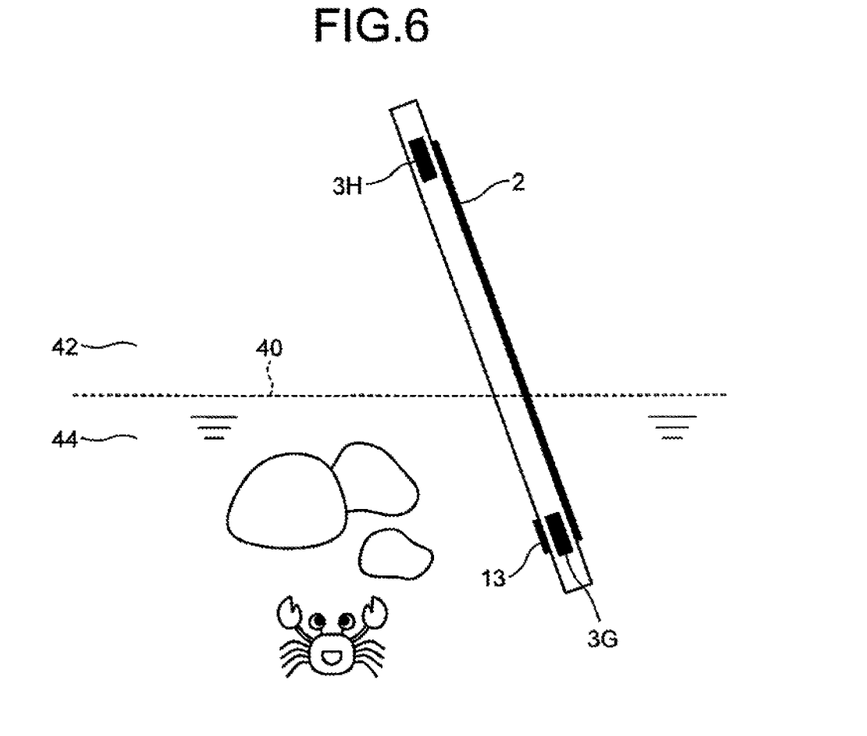
FIG. 6 is an explanatory diagram for explaining an example of the control performed by the smartphone according to the embodiments.
Figure 7:
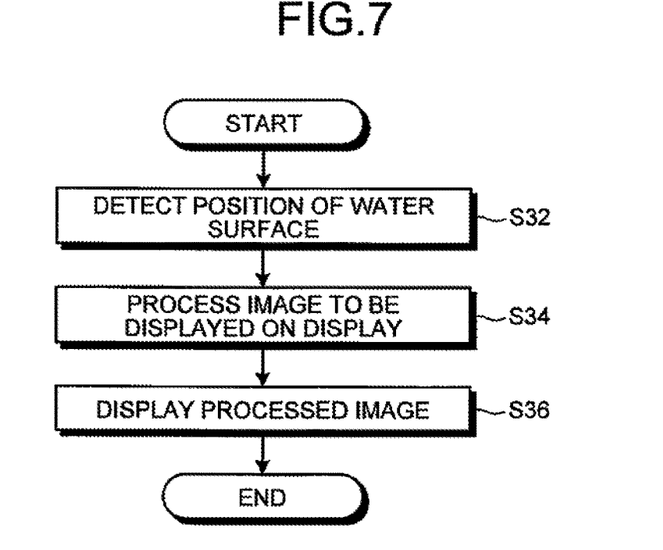
FIG. 7 is a flowchart illustrating an example of the control performed by the smartphone according to the embodiments.
Figure 10:
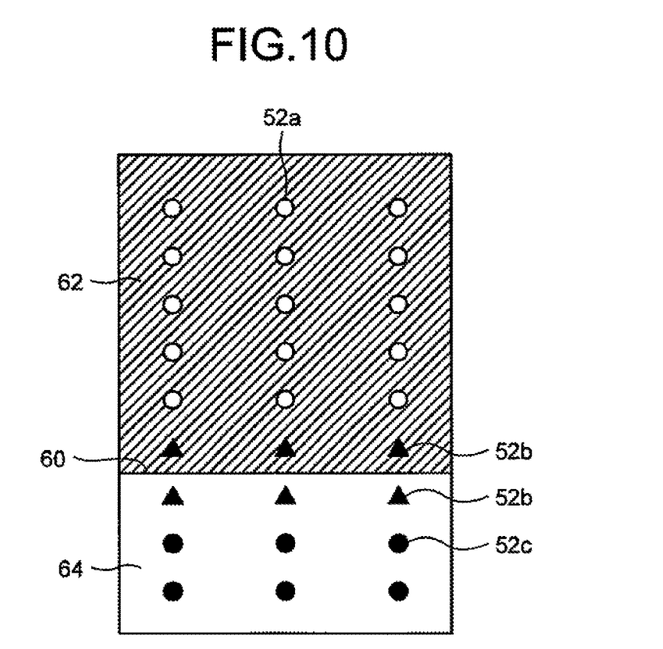
FIG. 10 is an explanatory diagram for explaining the processing of determining the position of the water surface.
Figure 11:
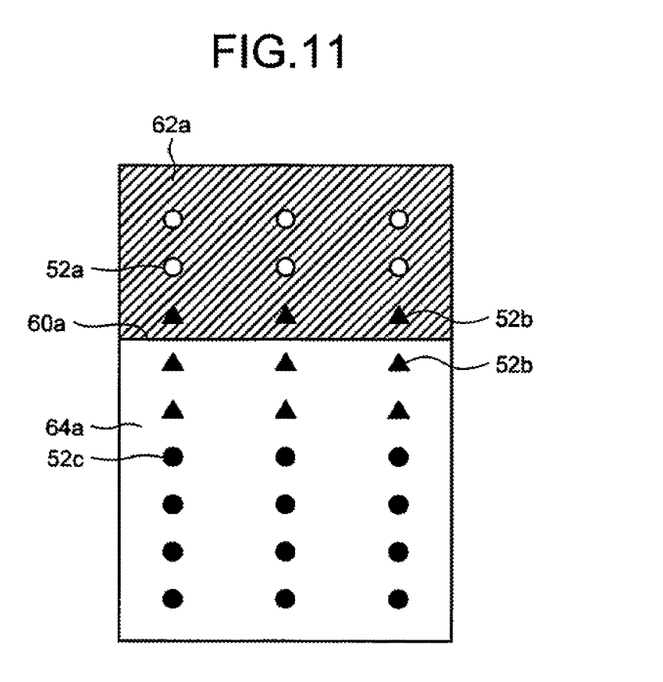
FIG. 11 is an explanatory diagram for explaining the processing of determining the position of the water surface.
Figure 12:
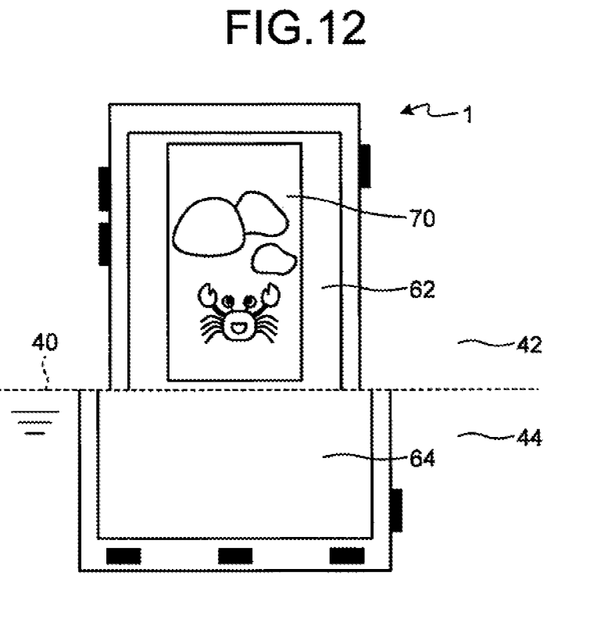
FIG. 12 is an explanatory diagram for explaining an example of an image to be displayed based on the position of the water surface.
Figure 13:
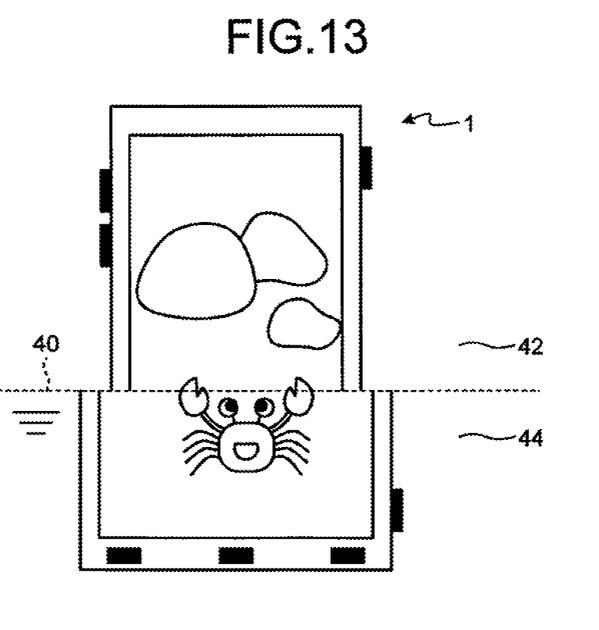
FIG. 13 is an explanatory diagram for explaining an example of the control performed by the smartphone according to the embodiments.

The control performed by the smartphone 1 will be explained next with reference to FIG. 5 to FIG. 13. FIG. 5 is a flowchart illustrating an example of the control performed by the smartphone according to the embodiments. FIG. 6 is an explanatory diagram for explaining an example of the control performed by the smartphone according to the embodiments. FIG. 7 is a flowchart illustrating an example of the control performed by the smartphone according to the embodiments. FIG. 8 to FIG. 11 are explanatory diagrams for explaining the processing of determining the position of a water surface. FIG. 12 is an explanatory diagram for explaining an example of an image to be displayed based on the position of the water surface. FIG. 13 is an explanatory diagram for explaining an example of the control performed by the smartphone according to the embodiments.

First of all, the controller 10 acquires results of the atmospheric pressure sensor 19 and the touch screen (touch sensor) 2B (Step S12). The controller 10 determines whether the smartphone 1 is in contact with water based on the detection results of the atmospheric pressure sensor 19 and the touch screen 2B. Here, the value detected by the atmospheric pressure sensor 19 increases if the smartphone (terminal) 1 is in contact with water. The controller 10 determines whether it is in contact with water based on the data stored in the atmospheric pressure data 9B and the change in the value of the atmospheric pressure. For example, when the change in the atmospheric pressure for a predetermined interval exceeds a predetermined threshold, the controller 10 determines that the state of the smartphone 1 is changed from not being in contact with water to being in contact with water. The controller 10 also determines whether it is in contact with water based on a sampling point detected by the touch screen 2B and an output value at the sampling point. Although the sampling point will be explained later, in the touch screen 2B, a charge value at the detected sampling point under the water greatly differs from a charge value at a sampling point above the water. The controller 10 can determine whether each of the sampling points is under the water or above the water based on the detection results of the touch screen 2B.

When acquiring the results of the atmospheric pressure sensor 19 and the touch screen (touch sensor) 2B, the controller 10 determines whether it is in contact with water (Step S14). When it is determined that it is not in contact with water (No at Step S14), the controller 10 sets a ground mode (Step S16).

When it is determined that it is in contact with water (Yes at Step S14), the controller 10 determines whether the whole of the smartphone 1 is in contact with water (Step S18).

The fact that the whole of the smartphone 1 is in contact with water mentioned here indicates that the smartphone 1 is in a position below the water surface. The fact that the smartphone 1 is in contact with water indicates a state in which the smartphone 1 is surrounded by water and a state in which the outer periphery of the housing 20 is filled with water.

Moreover, the fact that a part of the smartphone 1 is in contact with water indicates, as illustrated in FIG. 6, that an upper edge of the smartphone 1 in the vertical direction is above a water surface 40, i.e., is over the water 42, and that a lower edge of the smartphone 1 in the vertical direction is below the water surface 40, i.e., is under the water 44. The fact that a part of the smartphone 1 is in contact with water indicates that the part of the smartphone 1 is covered in water and the rest thereof is not covered in water, i.e., the smartphone 1 is in contact with the water surface. The controller 10 determines whether each of the sampling points is in contact with water based on the detection results of the touch screen 2B, and thereby can determine whether the part of the smartphone 1 is in contact with water. The smartphone 1 may be provided with a plurality of atmospheric pressure sensors 19 and determine whether a part of the smartphone 1 is in contact with water based on the detection results of the atmospheric pressure sensors 19.

When it is determined that the whole of the smartphone 1 is in contact with water (Yes at Step S18), the controller 10 sets an underwater mode (Step S20). When it is determined that the whole of the smartphone 1 is not in contact with water (No at Step S18), the controller 10 sets a partially underwater mode (Step S22).

The controller 10 sets the mode by switching between the ground mode, the underwater mode, and the partially underwater mode. When it is determined that the whole of the own device, i.e., the touch screen display 2 is above the water 42 based on the detection results of the sensors, the controller 10 sets the ground mode. When it is determined that the whole of the own device, i.e., the touch screen display 2 is under the water 44 based on the detection results of the sensors, the controller 10 sets the underwater mode. When it is determined that a part of the own device, i.e., the touch screen display 2 is above the water 42 and a part thereof is under the water 44 based on the detection results of the sensors, the controller 10 sets the partially underwater mode.

The controller 10 changes display rules of an image to be displayed on the display 2A depending on whether it is in the partially underwater mode or in any other mode.

Figure 8:
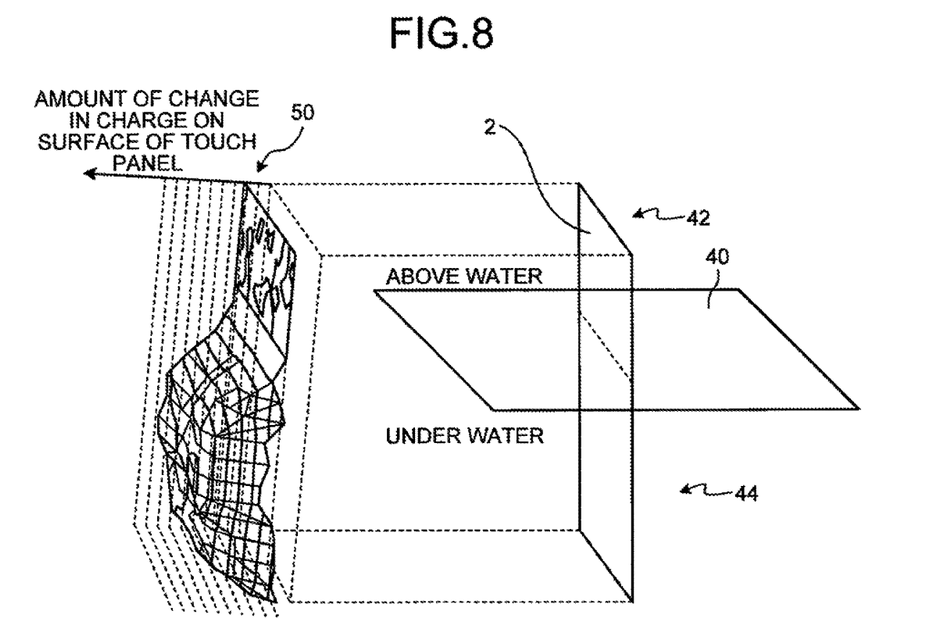
FIG. 8 is an explanatory diagram for explaining processing of determining a position of a water surface.

The change of the display rules of an image to be displayed on the display 2A in the partially underwater mode are explained with reference to FIG. 7 to FIG. 12. FIG. 7 is a flowchart illustrating an example of processing performed when it is determined that the mode is the partially underwater mode. The controller 10 detects the position of the water surface 40 (Step S32). As illustrated in FIG. 8, when the water surface 40 is positioned at the middle of the touch screen display 2, the amount of change in charge significantly differs, as illustrated in a graph 50, at a portion of the touch screen 2B under the water 44 and at a portion of the touch screen 2B above the water 42.

Figure 9:
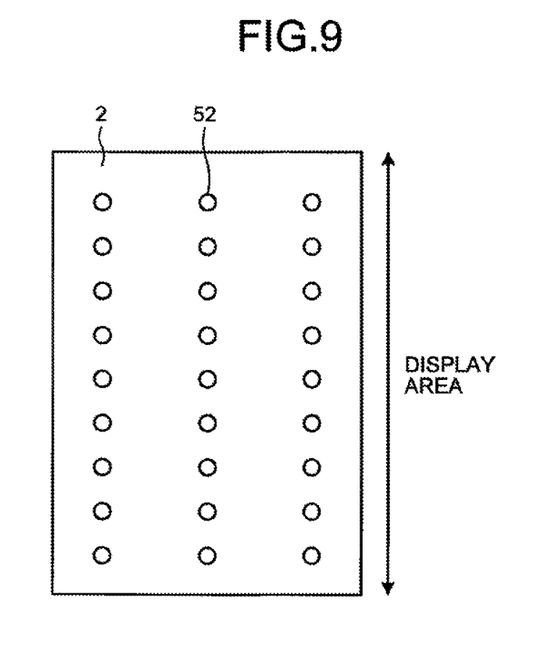
FIG. 9 is an explanatory diagram for explaining the processing of determining the position of the water surface.

As illustrated in FIG. 9, sampling points 52 are two-dimensionally arranged on the touch screen 2B. As illustrated in FIG. 10 and FIG. 11, the controller 10 determines that sampling points 52a are above the water 42 and determines that sampling points 52b are above the water 42 or under the water 44. When it is determined that sampling points 52c are under the water 44, the controller 10 detects lines 60 and 60a included in the sampling points 52b as a line of the water surface 40 respectively. The controller 10 determines areas 62 and 62a which include the sampling points 52a, of areas divided by the lines 60 and 60a respectively, as areas above the water 42 (areas where the touch screen 2B is not in contact with in water). The controller 10 determines area 64 and 64a which include the sampling points 52c, of the areas divided by the lines 60 and 60a respectively, as areas under the water 44. In this way, the controller 10 determines the positions of the lines 60 and 60a and the area state of the areas 62, 62a, 64, and 64a based on the distribution of the sampling points 52a, 52b, and 52c.

When detecting the position of the water surface 40, the controller 10 processes an image to be displayed on the screen (display) 2A (Step S34), and displays the processed image (Step S36).

Specifically, as illustrated in FIG. 12, the controller 10 performs processing for reducing an image to be displayed according to the size of the area 62 above the water 42. The controller 10 displays a reduced image 70 in the area 62. The image 70 may be so called a live view screen. In this case, although no image is displayed in the area 64, it is also possible to display a part of the image before being reduced or an image different from the reduced image therein.

In the cases of the ground mode and the underwater mode, the controller 10 displays an image to be displayed on the display 2A as it is without processing the image to be displayed based on the position of the water surface 40 as illustrated in FIG. 7.

As explained above, in the case of the partially underwater mode, the controller 10 can display the image more easily viewable for the user by displaying the image only in the area 62 above the water 42. In the conventional smartphone, when the image is displayed on the display 2A without processing the image, a part of the image under the water 42 appears bent by changing a refractive index at the water surface 40 as a boundary and the image visibility is low. On the other hand, since the smartphone 1 which is an example of the present embodiment displays the image only in the area 62 above the water 42, it is possible to prevent the image visibility from becoming low. Moreover, since the smartphone 1 displays the image only in the area 62 above the water 42, it is possible to prevent that the image in the area 64 under the water 44 is not visible and a part of the image cannot be recognized due to reflection on the water surface 40.

In the embodiments, the controller 10 performs the processing of displaying the processed image 70 in the area 62 above the water 42 and of not displaying the image in the area 64 under the water 44. However, the embodiments are not limited thereto. The controller 10 may also perform the processing of displaying the processed image in the area 64 under the water 44 and of not displaying the image in the area 62 above the water 42. In this case, the controller 10 is capable of displaying the image on the side where the user is easy to see the image when he/she stays under the water 44 and sees the display 2A. It is preferable that the controller 10 can select the area 62 or the area 64 as an area for displaying the image according to the setting of the user.

The embodiments have explained the case in which the controller 10 displays the image in either one of the area 62 and the area 64 and does not display the image in the other. However, the embodiments are not limited thereto. The controller 10 may be configured to enlarge an image to be displayed and display the enlarged image in the area 62. Specifically, the controller 10 may display an enlarged image of a part of an image to be displayed in the area 62 and display the rest of the image in the area 64. In this way, the controller 10 changes a display magnification of each of the images in the area 62 and the area 64, and can thereby change the image according to the change in appearance caused by optical refraction at the water surface 40. Thus, the smartphone 1 can suppress the changing of the image at the water surface 40 as illustrated in FIG. 13 even when the image is displayed in the partially underwater mode.

In the embodiments, the controller 10 enlarges the image in the area 62, but may reduce the image in the area 64.

In the embodiments, it is configured that, in the case of the partially underwater mode, the smartphone 1 displays the image to be displayed with being changed in a portion of the display 2A above the water and in a portion of the display 2A under the water based on the water surface 40 as a boundary therebetween, and in the cases of the underwater mode and the ground mode, displays the image in the entire surface of the display 2A based on one displaying rule. However, the embodiments are not limited thereto. The smartphone 1 may use different displaying rule for an orientation of an image to be displayed on the display 2A in the partially underwater mode, in the underwater mode and the ground mode respectively.

Figure 14:
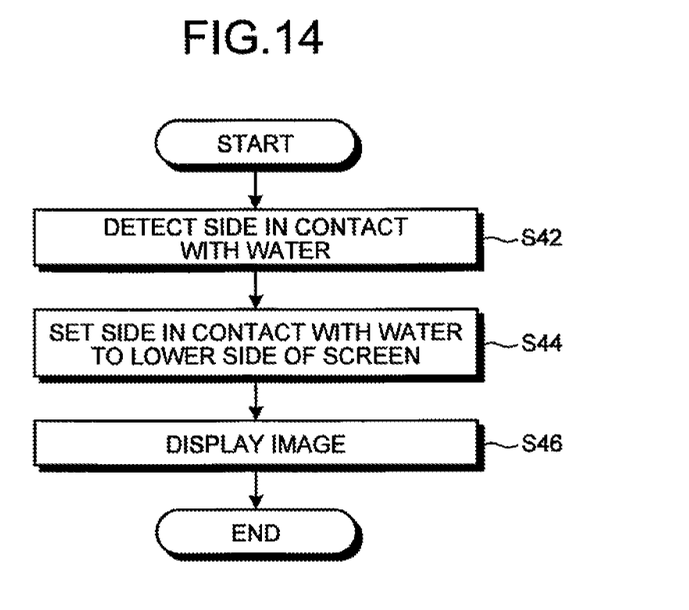
FIG. 14 is a flowchart illustrating an example of the control performed by the smartphone according to the embodiments.

FIG. 14 is a flowchart illustrating an example of the control performed by the smartphone according to the embodiments. FIG. 15 to FIG. 19 are explanatory diagrams for explaining examples of the control performed by the smartphone according to the embodiments.

As illustrated in FIG. 14, the controller 10 detects the side of the smartphone 1 in contact with in water (Step S42), sets the side of the smartphone 1 in contact with water to the lower side of the screen (Step S44), and displays an image in an orientation based on the setting (Step S46).

Figure 15:
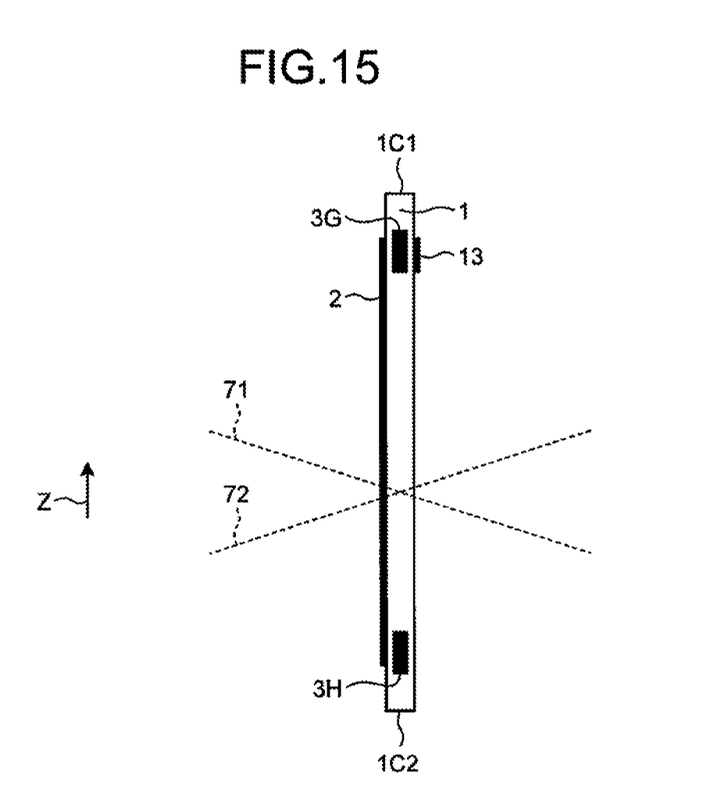
FIG. 15 is an explanatory diagram for explaining an example of the control performed by the smartphone according to the embodiments.

As illustrated in FIG. 15, the smartphone 1 is configured that an orientation of the housing 20 and the touch screen display 2, and a reference position for switching a display direction are defined to be set, based on a Z direction which is a vertical direction. The controller 10 can detect the orientation of the housing 20 and the touch screen display 2 with respect to the Z direction based on detection results of the acceleration sensor 15, the direction sensor 16, and the gyroscope 17.

Figure 16:
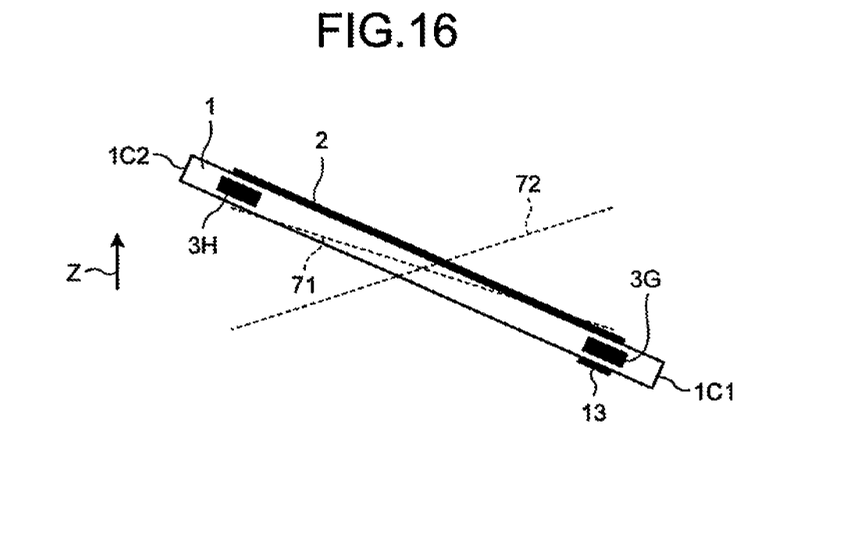
FIG. 16 is an explanatory diagram for explaining an example of the control performed by the smartphone according to the embodiments.

In the case of the ground mode or the underwater mode, the controller 10 changes the orientation of the image to be displayed in the display 2A based on reference lines 71 and 72. The reference line 71 illustrated in FIG. 15 is a reference line for rotating the smartphone 1 clockwise in a state in which the display 2A can be viewed from the upper side in the vertical direction. When the side face 1C1 is positioned at the upper side in the vertical direction, the smartphone 1 displays the image on the screen in which the side face 1C1 is defined to be set as the upper side of the screen. The smartphone 1 is more rotated clockwise in the state in which the display 2A can be viewed from the upper side in the vertical direction. Then, when the side face 1C1 is positioned lower than the side face 1C2 in the vertical direction and exceeds the reference line 71 as illustrated in FIG. 16, the controller 10 changes the orientation of the image to be displayed to an orientation in which the side face 1C2 corresponds to the upper side of the screen. Thereafter, the smartphone 1 is rotated counterclockwise in the state in which the display 2A can be viewed from the upper side in the vertical direction. Then, when the side face 1C2 is positioned lower than the side face 1C1 in the vertical direction and exceeds the reference line 72, the controller 10 changes the orientation of the image to be displayed to the orientation in which the side face 1C1 corresponds to the upper side of the screen.

Figure 17:
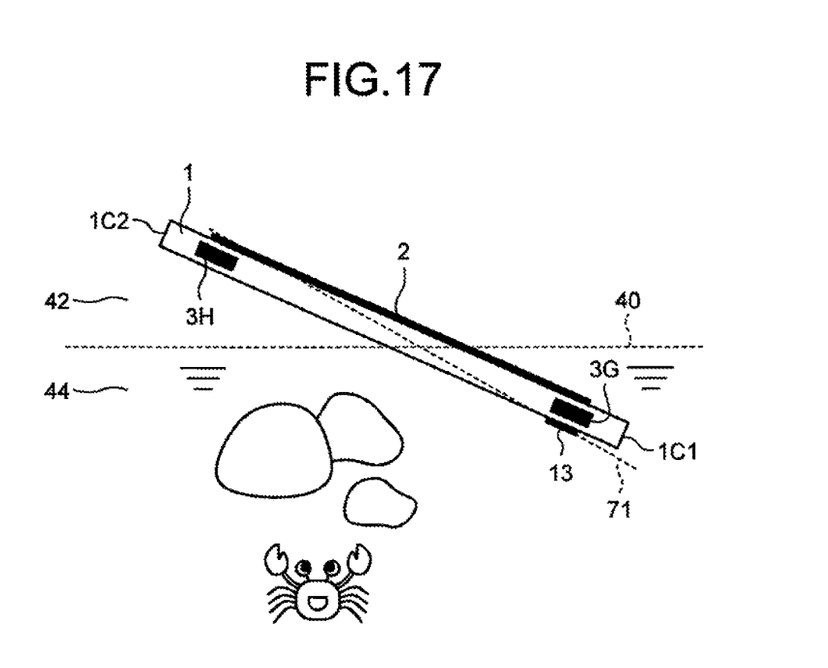
FIG. 17 is an explanatory diagram for explaining an example of the control performed by the smartphone according to the embodiments.
Figure 18:
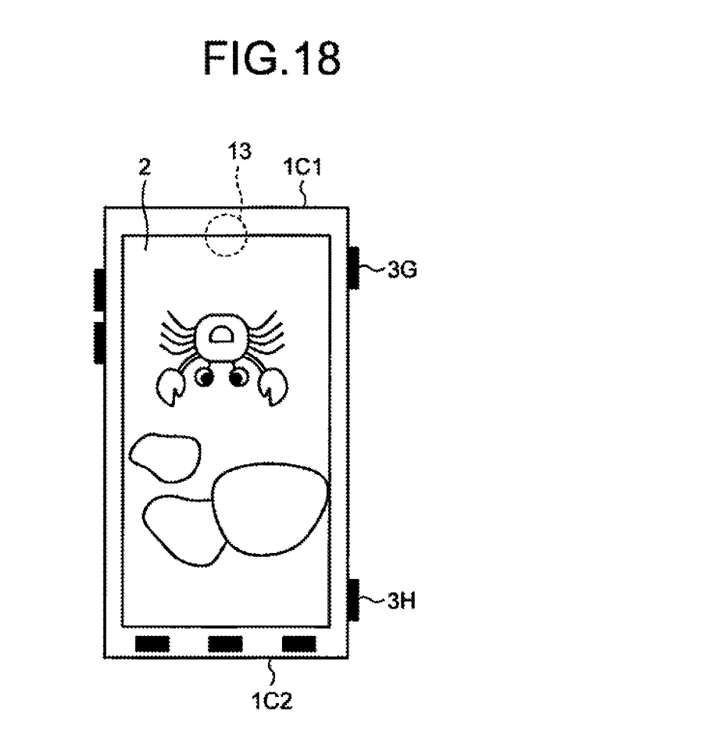
FIG. 18 is an explanatory diagram for explaining an example of the control performed by the smartphone according to the embodiments.
Figure 19:
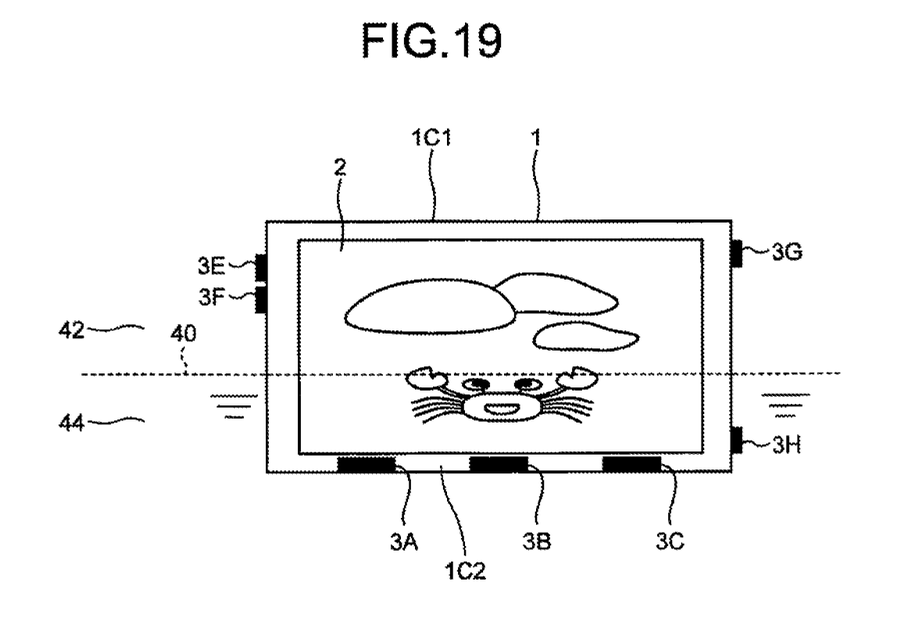
FIG. 19 is an explanatory diagram for explaining an example of the control performed by the smartphone according to the embodiments.

On the other hand, in the case of the partially underwater mode, when the display 2A in the side face 1C1 side is under the water 44 as illustrated in FIG. 17 even when the side face 1C1 does not exceed the reference line 71, the controller 10 displays the image in the orientation in which the side face 1C1 corresponds to the lower side of the screen, as illustrated in FIG. 18. Moreover, as illustrated in FIG. 19, when the display 2A in the side face 1C2 side is under the water 44, the controller 10 displays the image in the orientation in which the side face 1C2 corresponds to the lower side of the screen. The diagram illustrated in FIG. 19 is not a diagram visually recognized by the user above the water.

In this way, in the case of the partially underwater mode, by setting the side under the water 44 as the lower side of the screen, it is possible to prevent display of an inverted image.

The embodiments have explained the case in which a preview image is displayed on the display at the time of imaging but are not limited thereto. The controller 10 may associate information for the orientation of the image with image data acquired in such a manner that the side under the water 44 is defined to be set as the lower side of the screen, as illustrated in FIG. 14.

The embodiments disclosed in the present application can be modified. Moreover, the embodiments and modifications thereof disclosed in the present application can be combined with each other if necessary. For example, the embodiments may be modified as follows.

For example, the programs illustrated in FIG. 4 may be divided into a plurality of modules, or may be combined with any other program.

The embodiments have explained the smartphone as an example of the device with the touch screen. However, the device according to the appended claims is not limited to the smartphone. The device according to the appended claims may be any mobile electronic device other than the smartphone. Examples of the mobile electronic devices include, but are not limited to, a mobile phone, a tablet, a mobile personal computer, a digital camera, a media player, an electronic book reader, a navigator, and a game device.

Although the art of appended claims has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An electronic device, comprising:
  a display configured to display an image;
  at least one sensor configured to acquire information corresponding to a position of a water surface on the display; and
  at least one controller, wherein
  the at least one controller is configured to
    based on the position of the water surface on the display acquired by the at least one sensor, detect
      a first area of the display in contact with water, and
      a second area of the display not in contact with water, and
    when both the first area and the second area are detected,
      cause the display to display the image in both said the first and second areas, and
      enlarge a part of the image displayed within the second area.

2. The electronic device according to claim 1, further comprising:
  a housing; and
  an imaging device included in at least one end of a face of the housing, wherein
  the image is a live view screen of the imaging device.

3. The electronic device according to claim 1, further comprising:
  an inclination detector configured to detect an inclination of the electronic device with respect to a direction of gravity, wherein
  when the water surface is not detected on the display and both the first area and the second area are not detected,
    the at least one controller is configured to perform control of not changing an orientation of the image to be displayed on the display until the inclination of the electronic device detected by the inclination detector exceeds a predetermined angle range, and
  when the water surface is detected on the display and both the first area and the second area are detected,
    the at least one controller is configured to perform control of changing the orientation of the image to be displayed on the display so that a direction directed from the second area to the first area on the display corresponds to a downward direction even when the inclination of the electronic device detected by the inclination detector does not exceed the predetermined angle range.

4. The electronic device according to claim 1, further comprising:
  a housing; and
  an imaging device included in at least one end of a face of the housing.

5. The electronic device according to claim 1, wherein
  the at least one sensor includes a sensor configured to detect a change in capacitance, and
    output, in response to the detected change in capacitance, the information corresponding to the position of the water surface on the display between the first area in contact with water and the second area not in contact with water.

6. The electronic device according to claim 5, wherein
  the sensor configured to detect the change in capacitance is a touch sensor.

7. An image display method for controlling an electronic device with a display, the image display method comprising:
  displaying an image on the display;
  acquiring information corresponding to a position of a water surface on the display;
  based on the position of the water surface on the display acquired by said acquiring, detecting
    a first area of the display in contact with water, and
    a second area of the display not in contact with water; and
  when both the first area and the second area are detected, causing the display to display the image in both the first and second areas, and enlarging a part of the image displayed within the second area to compensate for image distortion due to optical refraction at the water surface.

8. A non-transitory storage medium that stores an image display program for causing, when executed by an electronic device with a display, the electronic device to execute:

displaying an image on the display;

acquiring information corresponding to a position of a water surface on the display;

based on the position of the water surface on the display acquired by said acquiring, detecting
a first area of the display in contact with water, and
a second area of the display not in contact with water; and adjusting the image so that the image is within the second area when both the first area and the second area are detected, wherein the electronic device includes:
a sensor configured to
detect a change in capacitance, and
output, in response to the detected change in capacitance, the information corresponding to the position of the water surface on the display between the first area in contact with water and the second area not in contact with water; and
an atmospheric pressure sensor configured to detect whether the electronic device is in contact with water.

9. The electronic device according to claim 2, wherein the controller is configured to determine existence of the first area on the display, even when the imaging device is located above the water surface.

10. The electronic device according to claim 1, wherein when both the first and second areas are detected, the at least one controller is configured to
enlarge the part of the image displayed within the second area to compensate for image distortion due to optical refraction at the water surface.

11. The electronic device according to claim 5, further comprising:
an atmospheric pressure sensor configured to detect whether the electronic device is in contact with water.

* * * * *